(12) United States Patent
Wada et al.

(10) Patent No.: US 6,436,081 B1
(45) Date of Patent: Aug. 20, 2002

(54) ABSORBENT ARTICLE WITH SURFACE STRUCTURE

(75) Inventors: Ichiro Wada; Yoshihisa Fujioka, both of Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 09/531,808

(22) Filed: Mar. 21, 2000

(30) Foreign Application Priority Data

Mar. 25, 1999 (JP) .......................................... 11-081966

(51) Int. Cl.[7] .............................................. A61F 13/15

(52) U.S. Cl. ........................... 604/385.01; 604/385.27; 604/385.16; 604/385.101

(58) Field of Search .................. 604/385.01, 385.16, 604/385.24, 385.26, 385.23, 385.27, 385.22, 385.101

(56) References Cited

U.S. PATENT DOCUMENTS

| | | | | |
|---|---|---|---|---|
| 3,542,027 A | * | 11/1970 | Higgins ....................... 128/284 |
| 4,685,914 A | * | 8/1987 | Holtman ...................... 604/368 |
| 4,895,568 A | * | 1/1990 | Enloe ......................... 604/385.2 |
| 5,181,563 A | * | 1/1993 | Amaral ....................... 604/385.2 |
| 5,964,743 A | * | 10/1999 | Abuto et al. ................. 604/385.1 |
| 6,056,732 A | * | 5/2000 | Fujioka et al. ............... 604/385.1 |
| 6,096,016 A | * | 8/2000 | Tsuji et al. .................. 604/378 |
| 6,099,515 A | * | 8/2000 | Sugito ....................... 604/385.1 |

FOREIGN PATENT DOCUMENTS

| | | |
|---|---|---|
| DE | 44 22 956 | 4/1996 |
| EP | 0366 079 | 5/1990 |
| EP | 0 685 212 | 12/1995 |
| GB | 2 042 343 | 9/1980 |
| GB | 2 284 831 | 6/1995 |
| JP | 6-70957 | 3/1994 |
| WO | WO 98/29074 | 7/1998 |

* cited by examiner

Primary Examiner—John G. Weiss
Assistant Examiner—Jacqueline Stephens
(74) Attorney, Agent, or Firm—Milbank, Tweed, Hadley & McCloy LLP (57) ABSTRACT

There is disclosed an absorbent article including: a surface structure having a liquid-permeable surface sheet located on a liquid-receiving side; a back sheet; and an absorbent core sandwiched between the surface structure and the back sheet. In an area including at least a centerline extending in a longitudinal direction of the absorbent article, the surface sheet is corrugated to form recesses and ridges extending in the longitudinal direction and alternating with each other in a transverse direction perpendicular to the longitudinal direction. The ridges are given an elastically shrinking function in the longitudinal direction at least at their crests or vicinities thereof so that the surface structure is formed into a curved shape. The surface structure thus curved can fit the shape of a crotch. Therefore, the liquid is hard to flow in the transverse direction to prevent the leakage.

7 Claims, 7 Drawing Sheets

ABSORBENT ARTICLE WITH SURFACE STRUCTURE

BACKGROUND OF THE INVENTION

1. Field of the Invention

The present invention relates to an absorbent article such as a disposable diaper, a pad for the incontinence of urine or a sanitary napkin and, more particularly, it relates to an absorbent article including a surface structure having an excellent fittingness on a body.

2. Related Art

The absorbent article of the prior art such as the disposable diaper, the pad for the urinary incontinence or the sanitary napkin generally includes: a liquid-permeable top sheet disposed on the liquid-receiving, inner side; a liquid-impermeable back sheet disposed on the outer side; and an absorbent core made of pulp and a highly absorbent polymer (or super absorbent polymer: SAP) and sandwiched between the two sheets.

In such an absorbent article, a structure has been investigated for improving the fittingness on a urinary organ and thereabout, when applied to a crotch, to prevent excreted liquid such as urine or menstrual blood from leaking transversely. For example, there has been practiced a structure, in which a relatively bulky cushion layer made of a hydrophilic fiber layer is disposed on the liquid-receiving side of the absorbent core, or a structure in which an absorbent material layer smaller than the absorbent core is disposed on the liquid-receiving side of the absorbent and such a cushion layer as above is further disposed on the absorbent material layer. In another structure, gathers for preventing the transverse leakage are disposed on two side edges of the absorbent core.

However, the aforementioned absorbent article provided with the cushion layer cannot cover the individual differences in the shape of the crotch reliably at all times. Especially, the disposable diaper or the pad for the urinary incontinent for taking care of old people frequently fails to fit the crotch. This is because the old people are seriously different among the individuals in the width of the crotch, in the flesh of the crotch, abdomen or hip or in the flabbiness or wrinkles of the skin, as compared with infants. If the absorbent article fails to fit the crotch, the excreted liquid will easily leak along the skin to the outside of the absorbent article to wet the wears or bedclothes. This problem is more serious for the old people who excrete far more liquid for one piss than the infants. When such an absorbent article unfitted for the crotch is worn, moreover, irregular wrinkles are formed on the liquid-receiving side of the absorbent article to make it harder for the absorbent article to absorb the excreted liquid.

Against these problems, there exists an absorbent article which is curved to fit the crotch by providing transverse leakage preventing gathers on two side edges of an absorbent core so that the absorbent core may follow the gathers. However, even in this absorbent article, because the central portion of the absorbent core is less curved than the side edges thereof, the absorbent core is difficult to fit the whole crotch, thereby to leave gaps between the absorbent core and the crotch. As a result, a large amount of excreted liquid may move transversely through the gaps so that its leakage cannot be prevented by the transverse leakage preventing gathers.

SUMMARY OF THE INVENTION

The present invention is to solve the problems of the prior art thus far described and has an object to provide an absorbent article in which a surface structure disposed on the liquid-receiving side easily fits the crotch, the urinary organ or the inguinal region.

Another object of the invention is to provide an absorbent article which is so curved as to easily fit the crotch of the wearer thereby to prevent the transverse leakage of the excreted liquid.

According to an aspect of the invention, there is provided an absorbent article comprising: a surface structure having a liquid-permeable surface sheet located on a liquid-receiving side; a back sheet; and an absorbent core sandwiched between the surface structure and the back sheet, wherein, in an area including at least a centerline extending in a longitudinal direction of the absorbent article, the surface sheet is corrugated to form recesses and ridges extending in the longitudinal direction and alternating with each other in a transverse direction perpendicular to the longitudinal direction, and the ridges are given an elastically shrinking function in the longitudinal direction at least at their crests or vicinities thereof so that the surface structure is formed into a curved shape.

With the surface structure of the absorbent article of the invention, the surface sheet constructing the surface structure elastically shrinks in the longitudinal direction so that the surface structure is curved. As a result, the absorbent article is curved in its entirety so that the liquid-receiving side easily fits the crotch, the abdomen or the back (or hip). Therefore, the excreted liquid can be quickly absorbed by the absorbent article while being prevented from leaking transversly. To give the elastically shrinking function, preferably, elastic members extending in the longitudinal direction are attached to the crests of the ridges of the surface sheet.

Moreover, because the ridges thus formed have degrees of freedom against the vertical and horizontal pressures i.e., because they can be flexibly deformed, the ridges can fit the roughness of the urinary organ, the crotch or the inguinal region. In other words, the surface structure comes into contact with the wearer's body to have a larger contact area for eliminating gaps between the absorbent article and the wearer's body. As a result, the excreted liquid is prevented from flowing transversely in such gaps and its leakage is further reduced.

Preferably, the surface structure further includes a liquid-permeable support sheet located between the surface sheet and the absorbent core, and the support sheet is bonded to the surface sheet at an interval in the transverse direction to thereby form the recesses. In this case, more preferably, a cushion layer is provided inside of the ridges such that the cushion layer is sandwiched between the surface sheet and the support sheet.

Preferably, ridges in a center region including the longitudinally extending centerline are different in height from other ridges in two side regions outside of the center region.

Preferably, cover sheets are provided to cover longitudinal end portions of the ridges.

DESCRIPTION OF THE PREFERRED EMBODIMENTS

Figure 1:
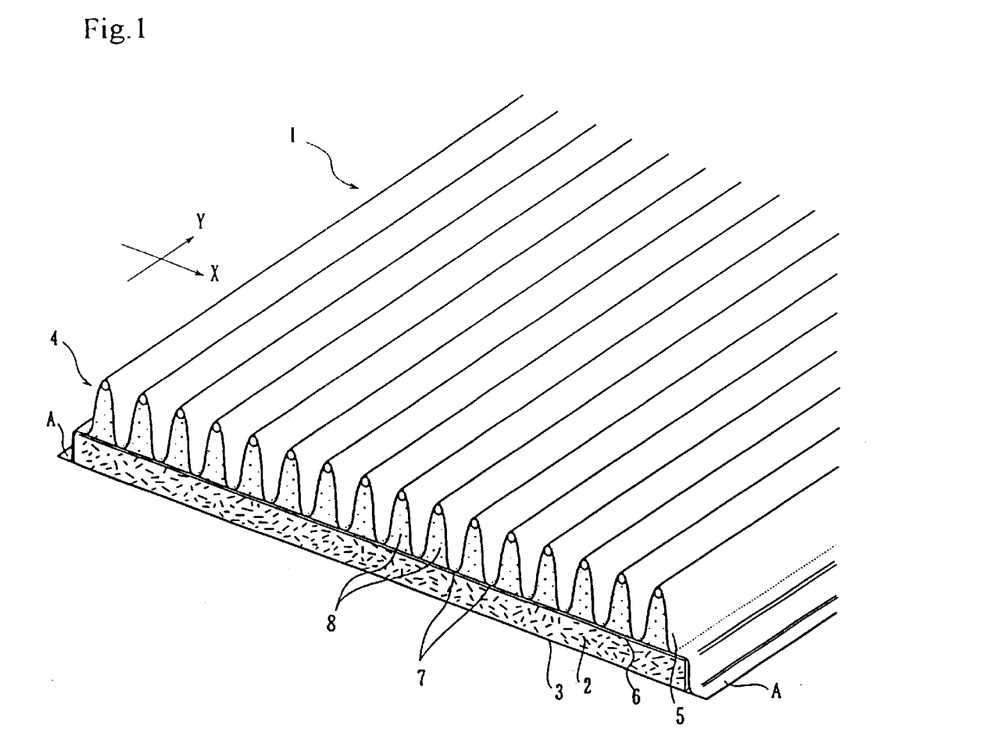
FIG. 1 is a partially sectional, perspective view showing an absorbent article according to a first embodiment of the invention.
Figure 2:
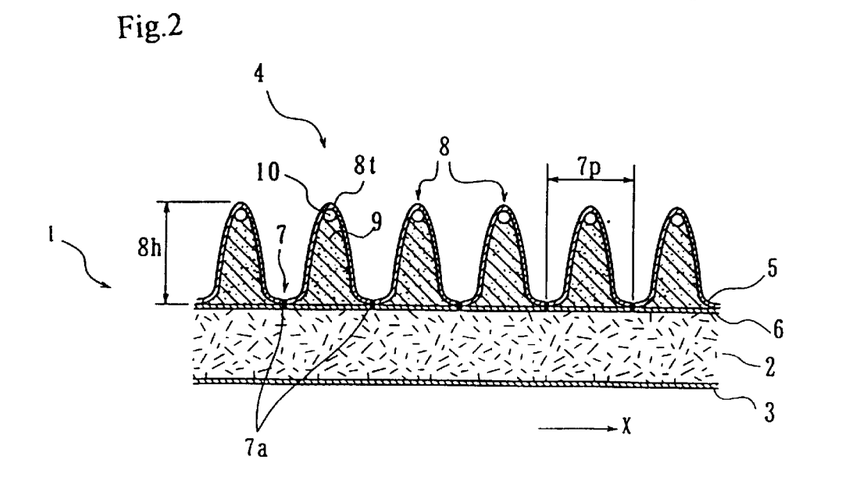
FIG. 2 is a sectional view of the absorbent article shown in FIG. 1.
Figure 3:
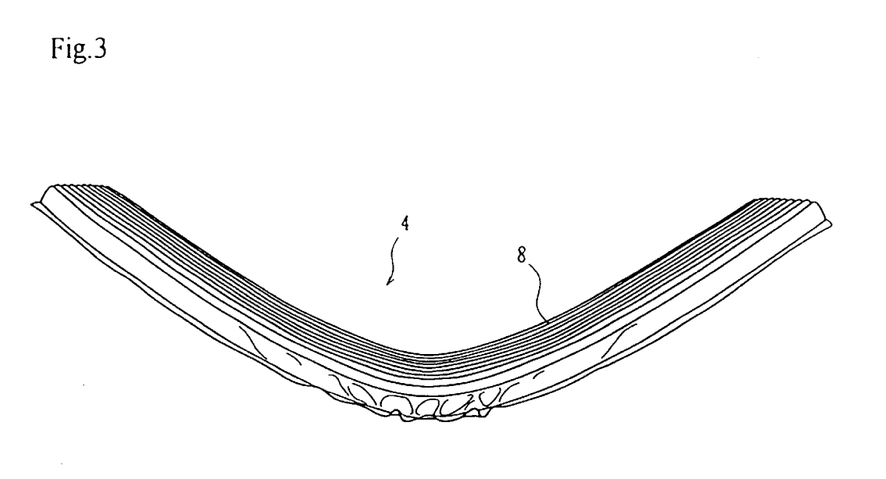
FIG. 3 is an explanatory view showing a curved state of a surface structure of the invention.

FIG. 1 is a partially sectional, perspective view showing an absorbent article according to a first embodiment of the invention; FIG. 2 is a sectional view of the absorbent article of the invention; and FIG. 3 is an explanatory view showing a state in which a surface structure is curved. In the following, a direction X is a transverse (or widthwise) direction of the absorbent article, and a direction Y is a longitudinal (or lengthwise) direction of the absorbent article.

As shown in FIGS. 1 and 2, an absorbent article 1 is backed on a back side of an absorbent core 2 with a back sheet 3 and is surfaced on a liquid-receiving side of the absorbent core 2 with a surface structure 4. This surface structure 4 includes a surface sheet 5 and a support sheet 6, and these surface sheet 5 and support sheet 6 and the back sheet 3 are adhered together with an adhesive such as hot melt adhesive in a peripheral region A where no absorbent core 2 is present. When the surface sheet 5, the support sheet 6 and the back sheet 3 contain thermoplastic fibers, they may be thermally fused together in the aforementioned peripheral region A. Alternatively, it may be possible that only the support sheet 6 and the back sheet 3 are bonded (adhered or fused) together in the peripheral region A, while the surface sheet 5 is bonded to the support sheet 6 at a position inside of the peripheral region A (i.e. at a positon where the absorbent core 2 is present).

The absorbent core 2 is constructed by enveloping either pulverized pulp or a mixture of pulverized pulp and highly absorbent polymer (or super absorbent polymer: SAP) with an absorbent sheet such as tissue paper. The SAP can be made of polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like. Examples of the SAPs include: a cross-linked compound of sodium polyacrylate, a graft copolymer of starch having sodium polyacrylate or a graft copolymer of cellulose having polyacrylonitrile chains. The back sheet 3 may be liquid-impermeable and made of, for example, an olefin resin sheet. When the absorbent article I is used as a disposable diaper or sanitary napkin, the back sheet 3 is preferably made gas-permeable. However, the back sheet 3 of the absorbent article 1 of the invention may be made liquid-permeable, if it is used to be worn inside another absorbent material in which excessive liquid will permeate and will be absorbed.

The aforementioned surface sheet 5 and support sheet 6 composing the surface structure 4 are preferably made of a point-bond, air-through, spun-bond or spun-lace non-woven fabric. This non-woven fabric is formed of, for example, hydrophilized hydrophobic fibers or hydrophilic fibers. The "hydrophilized hydrophobic fibers" as used herein means hydrophobic fibers subjected to hydrophilic treatment. In this hydrophilic treatment, a hydrophobic fiber is made hydrophilic by treating it with a surfactant; by chemically binding a chemical substance such as a monomer or a polymer having a hydrophilic group thereto; by subjecting it to plasma processing; by kneading it with a chemical substance having a hydrophilic group; or by treating its surface to have a profiled section. The surface sheet 5 and support sheet 6 may be made of a resin film having a number of apertures. This resin film can be made of polyethylene (PE) or the like.

As in FIG. 2, the surface sheet 5 is bonded to the support sheet 6 at an interval (or pitch distance) 7p in the transverse direction. These bonded portions are designated by 7a. By forming these bonded portions 7a, the surface sheet 5 is corrugated to have recesses 7 and ridges 8. That is, the surface sheet 5 is deformed to have the ridges (or bulges) 8 rising toward the wearer, between the bonded portions 7a. The ridges 8 and the recesses 7 are extended in the longitudinal direction (or the direction Y) to form a plurality of parallel rows. The bonding between the surface sheet 5 and the support sheet 6 for forming the recesses 7 can be performed by adhesion with an adhesive such as hot melt adhesive. Alternatively, the surface sheet 5 and the support sheet 6 may be thermally fused together when they contain thermoplastic fibers.

The bonded portions 7a may be formed in longitudinally continuous lines. Alternatively, they may be formed to extend intermittently in the longitudinal direction. For example, if an adhesive of the hot melt type is applied to the surface of the support sheet 6 in a spiral pattern or the like and the surface sheet 5 is adhered to the support sheet 6, the bonded portions 7a can be formed intermittently in the longitudinal direction as above. When the bonded portions 7a are thus intermittently formed, the excreted liquid such as urine fed to the recesses 7 readily penetrates from the bottoms of the recesses 7 into the absorbent core 2.

At the crests 8t of the ridges 8, there are arranged elastic members 10, each extending in the longitudinal direction. These elastic members 10 are adhered to the inner side of the surface sheet 5, i.e., to the face of the surface sheet 5 on the side of the absorbent core 2, while being elongated (or pulled and stretched) in the longitudinal direction. Therefore, after such adhesion, the surface sheet 5 longitudinally shrinks at the crests 8t owing to the elastically shrinking function of the elastic members 10, so that the whole surface structure 4 is curved as shown in FIG. 3. As a result, the absorbent core 2 is also curved.

The elastic members 10 may be made of any elastic material such as natural rubber, synthetic rubber or stretch non-woven fabric (i.e., non-woven fabric having elasticity).

Here, the surface sheet 5 per se may be made of such stretch non-woven fabric to have an elastically shrinking function in the longitudinal direction. In this case, the elastic members 10 need not be provided to the surface sheet 5. Therefore, the surface structure 4 can be easily manufactured.

The height of the ridges 8, that is, the height size 8h (as referred to FIG. 2) from the surface of the support sheet 6 to the crests 8t of the ridges 8 is preferably from 5 mm or more to 50 mm or less. Within this range, the liquid-receiving side of the absorbent article can fit the crotch of a wearer, even if the absorbent article is used for taking care of old people who are seriously different among the individuals in body contours. More preferably, the height size 8h is from 10 mm or more to 30 mm or less.

In the surface structure 4, moreover, there may be provided a cushion layer 9 of a hydrophilic material inside of the ridges 8, i.e., between the surface sheet 5 and the support sheet 6, as shown in FIGS. 1 and 2. With this cushion layer 9, the elastcity of the ridges 8 is so enhanced that the shape of the ridges 8 can be maintained securely when they come into contact with the wearer. In this case, therefore, the surface structure 4 will fit the crotch more closely. In stead of providing the cushions layer 9, however, the inside of the ridges 8 may be vacant. That is, the space between the surface sheet 5 and the support sheet 6 may be left as clear gaps.

The hydrophilic material for the cushion layer 9 can be exemplified by various materials. For example, use can be made of hydrophilized hydrophobic fibers of polyethylene, polypropylene, nylon or polyester, hydrophilized hydrophobic composite fibers of polyester and polyethylene, or hydrophilic fibers such as rayon. As described before, the term "hydrophilized hydrophobic fibers" means hydrophobic fibers subjected to hydrophilic treatment. Such fibers may be long fibers (or filaments) prepared in the form of tow. Or else, use can be made of a split yarn or strip-shaped materials, which are originally hydrophilic or originally hydrophobic but subjected to hydrophilic treatment. The split yarn is produced by finely cutting a resin film into the net-like shape, in which short fibers extend generally in one direction. The strip-shaped materials are produced by cutting a resin film or nonwoven fabric into strips. Alternatively, the material may be exemplified by either a non-woven fabric, such as air-through non-woven fabric of hydrophilic fibers or hydrophobic fibers subjected to hydrophilic treatment, which is bulky and has a low density, or a web of opened fibers having a relatively short length (e.g., hydrophilic fibers or hydrophobic fibers subjected to hydrophilic treatment). Preferably, the cushion layer 9 is bulky and readily permeable to liquid and can be readily elastically recovered (or restored) from its pressurized state. Therefore, it is preferable that the cushion layer 9 has a density of 0.4 g/cm$^3$ or less and the fibers constituting the cushion layer 9 has a fineness of 1 denier or more.

Figure 4:
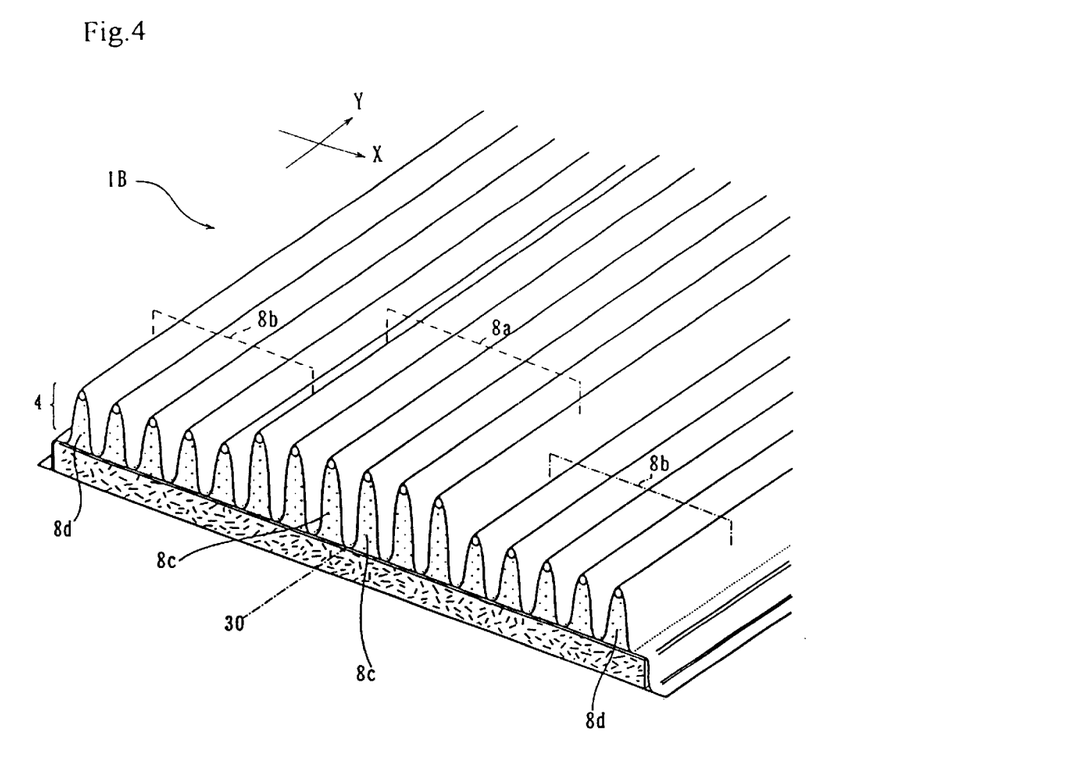
FIG. 4 is a partially sectional, perspective view showing an absorbent article according to a second embodiment of the invention.

FIG. 4 is a perspective view showing an absorbent article 1B of a second embodiment of the invention. In this absorbent article 1B, the ridges 8 are made different. Hereinafter, the detailed description of the portions having the same constructions as those of the first embodiment will be omitted by designating them by the common reference numerals.

In the embodiment shown in FIG. 4, the ridges 8 are made higher, as indicated by 8a, in the vicinity of the central region and made lower, as indicated by 8b, in the two side regions. Thus, the fittingness on the crotch or urinary organ is further enhanced by the difference of the height between the ridges 8a and 8b. In this case, the ridges 8a preferably have a height of about 25 mm whereas the ridges 8b preferably have a height of about 15 mm. This embodiment may be modified such that the ridges are gradually lowered from ridges 8c and 8c in the central region to ridges 8d and 8d in the two side regions.

On the contrary, the ridges 8a in the vicinity of the central region may be made lower whereas the ridges 8b in the two side regions may be made higher. In this case, the ridges 8a preferably have a height of about 5 mm whereas the ridges 8b preferably have a height of about 15 mm. Alternatively, the ridges 8 may be made gradually higher from the central region to the two side regions.

Figure 5:
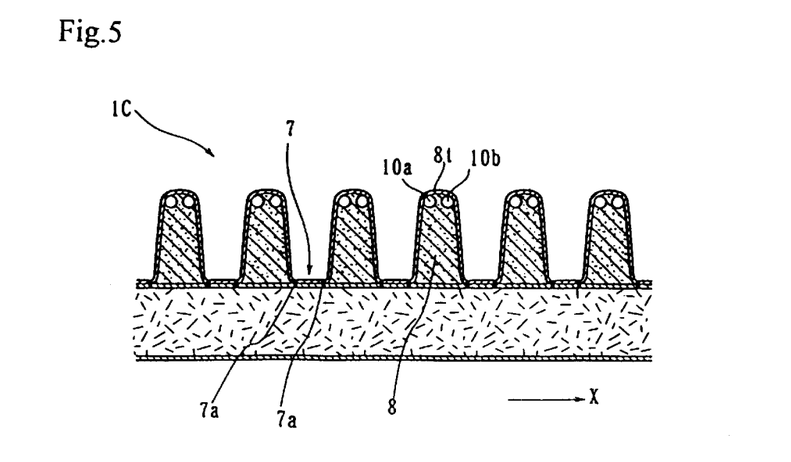
FIG. 5 is a sectional view showing an absorbent article according to a third embodiment of the invention.

FIG. 5 is a sectional view showing an absorbent article 1C of a third embodiment of the invention. In FIG. 5, two elastic members 10a and 10b are disposed at the crest 8t of each ridge 8. Between two adjacent ridges 8 and 8, on the other hand, two bonded portions 7a and 7a are provided to form one recess 7. That is, in each recess 7, two continuous or intermittent lines of the bonded portions 7a extend parallel to each other.

Figure 6:
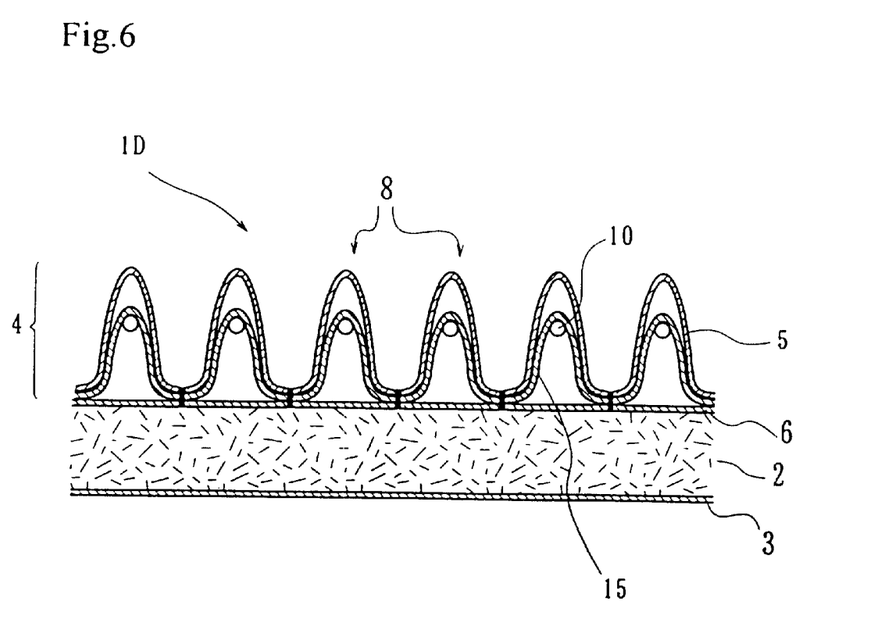
FIG. 6 is a sectional view showing an absorbent article according to a fourth embodiment of the invention.

FIG. 6 is a sectional view showing an absorbent article 1D of a fourth embodiment of the invention. In this embodiment, the ridge 8 is provided with additional inner ridges.

In this absorbent article 1D, a second surface sheet 15 having a liquid permeability is disposed on the inner side of the surface sheet 5 to form the inner ridges. Moreover, the elastic members 10 are disposed on the inner side of the second surface sheet 15, not on the inner side of the first surface sheet 5, i.e., at the crests of the inner ridges formed of the second surface sheet 15. With the second surface sheet 15, the cushioning properties of the surface structure 4 can be so enhanced without the aforementioned cushion layer 9 as to ensure a soft fitting on the crotch. In addition, the second surface sheet 15 functions as a liquid stopping layer for stopping liquid from flowing in the transverse direction . The second surface sheet 15 is formed of a resin film or a hydrophobic non-woven fabric having a plurality of apertures at a rate of aperture area of 30 to 50%, for example.

Here, the elastic members 10 may be disposed at the crests of the outer ridges of the first surface sheet 5, as in the first embodiment. It is also possible that the second surface sheet 15 per se is made of stretch non-woven fabric having the elastically shrinking function in the longitudinal direction while eliminating the elastic members 10. In this case, the first surface sheet 5 need not have the elastically shrinking function.

Figure 7:
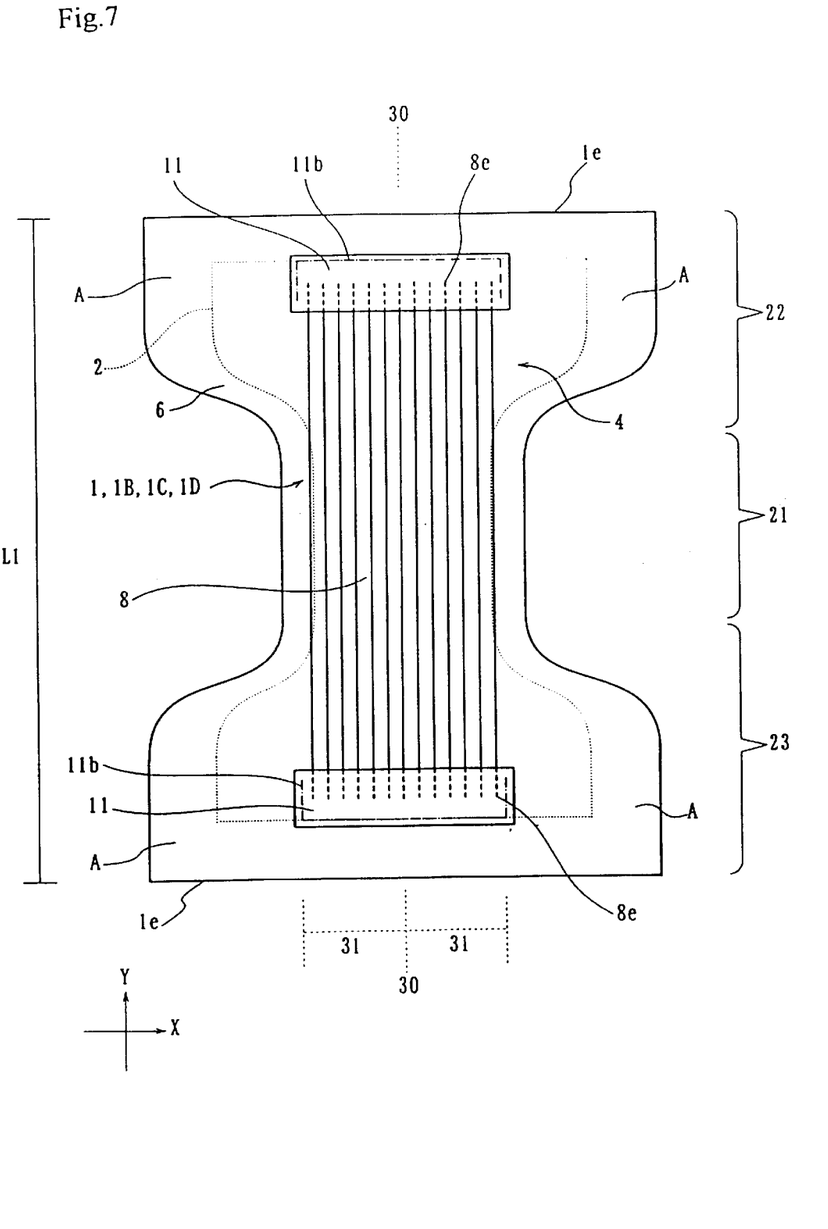
FIG. 7 is a top plan view showing an example in which a disposable diaper is constructed of the absorbent article of the invention.

FIG. 7 is a top plan view showing an open type disposable diaper with its liquid-receiving side being located on this side, as a specific embodiment of the absorbent article 1, 1B, 1C or 1D of the invention.

The disposable diaper, as constructed of the absorbent article of the invention, has: an intermediate portion 21 to be applied to the crotch of a wearer; a front portion 22 to be applied to the abdomen thereof; and a rear portion 23 to be applied to the hip thereof.

In the disposable diaper shown in FIG. 7, the back sheet 3 and the support sheet 6 are given an hour glass shape, and the absorbent core 2 (indicated by dotted lines in FIG. 7) is also given an hour glass shape. The transversely constricted portions of those hour glass shapes provide the aforementioned intermediate portion 21. In the peripheral region A where the absorbent core 2 is not present, the support sheet 6 and the back sheet 3 are bonded to each other to secure the absorbent core 2 therebetween.

In the disposable diaper shown in FIG. 7, the surface sheet 5 shown in FIGS. 1 and 2 is present only in the widthwise center on the liquid-receiving side to form the ridges 8 and the recesses 7. The cushion layer 9 may or may not be disposed between the surface sheet 5 and the support sheet 6.

The area where the ridges 8 and the recesses 7 are present is in a rectangular shape extending from the front portion 22 through the intermediate portion 21 to the rear portion 23 in the longitudinal direction and over two side regions 31 and 31 across a centerline 30 in the transverse direction. That is, as shown in FIG. 7, the ridges 8 and the recesses 7 are present in the area having a length almost equal to that of the absorbent core 2 and a width almost equal to that of the intermediate portion 21 of the absorbent core 2. The area may be modified variously according to the applications. In the disposable diaper of FIG. 7, the crests 8t of the ridges 8 of the surface sheet 5 are provided with the elastic members 10 for allowing the disposable diaper to be curved in its entirety by their elastic shrinking forces.

The elastic members 10 may be provided either all over the ridges 8 in the longitudinal direction or only over the intermediate portion 21 in the longitudinal direction. It may be also possible that not all but some of the ridges 8 are provided with the elastic members 10.

In order to make the curvature of the surface structure proper for the invention, the elastic members 10 are preferably provided over at least 10% of the entire length L1 of the absorbent article 1. However, the elastic members 10 should not be limited to a continuous length of 10% or more but may be provided partially, for example, at two portions of 5% or more of the entire length L1. The portion requiring the curvature is different for targets of application. For a baby or child, for example, it is preferable that not only the intermediate portion 21 but also both the front portion 22 and the rear portion 23 are curved to fit the round abdomen and hip. For an old wearer, the front portion 22 need not be curved. Thus, the portion to be curved is properly adjusted.

The ridges 8 of the surface structure 4 are covered at their opposite end portions 8e and 8e with cover sheets 11 and 11, as shown in FIG. 7. Preferably, each cover sheet 11 has a width larger than that of the area where the ridges 8 are formed, and is bonded to the support sheet 6 with a C-shaped bonded portion 11b to be opened toward the intermediate portion 21. That is, for forming a pocket, it is preferable that each cover sheet 11 is not bonded to the support sheet 6 on the side of the intermediate portion 21.

When the excreted liquid moves along the ridges 8, it flows to the front portion 22 or the rear portion 23 of the absorbent article 1 and may further flow to the end portions 1e and 1e of the absorbent article 1. With the cover sheets 11, however, the longitudinal flows are stopped and sealed by the pockets so that no excreted liquid leaks from the end portions 8e of the ridges 8. Moreover, the cover sheets 11 hide the end portions 8e of the ridges 8 to provide a beautiful appearance. The cover sheets 11 are preferably made of a hydrophobic sheet having a basis weight (This may be referred to as "METSUKE" in Japanese measuring unit) of 20 g/m² or more, such as a spun-bond non-woven fabric, a point-bond non-woven fabric, a non-woven fabric laminated with polyethylene, or a film.

Figure 8:
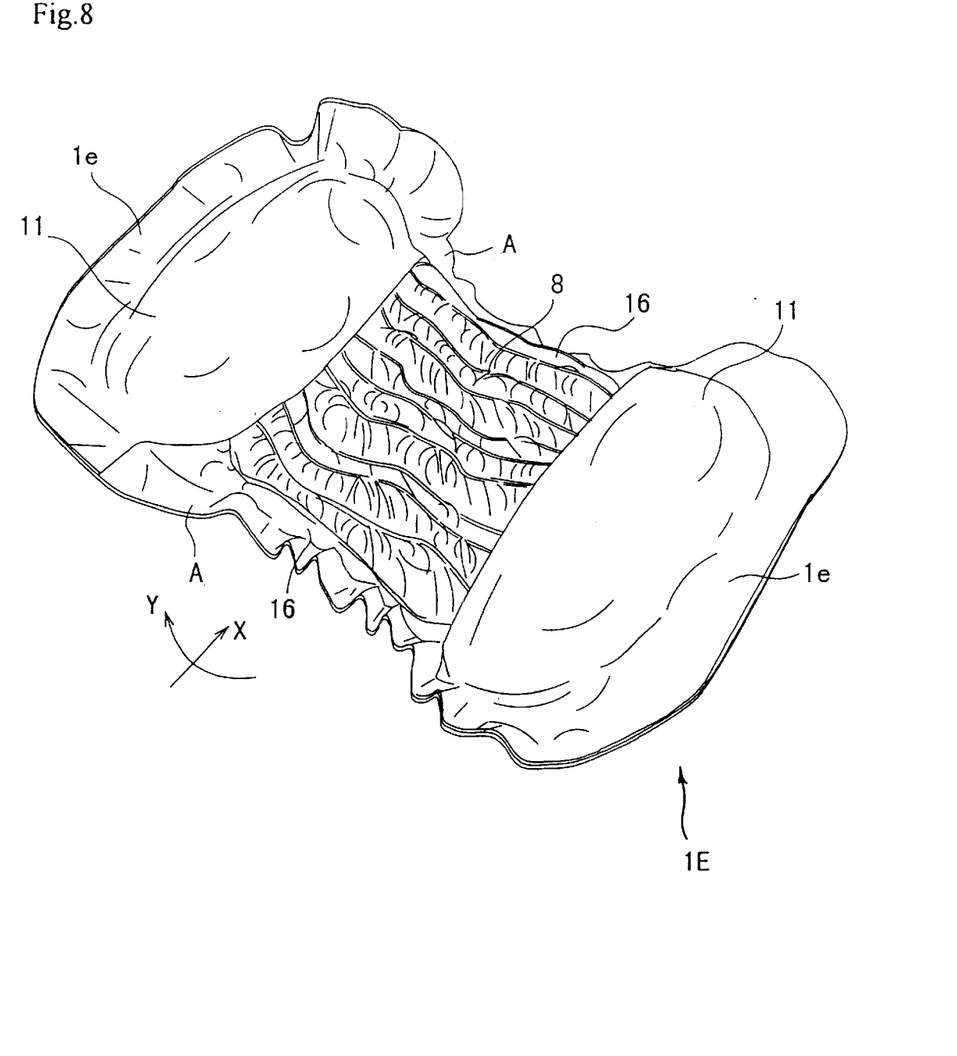
FIG. 8 is a perspective view showing an absorbent article according to a fifth embodiment of the invention.
Figure 9:
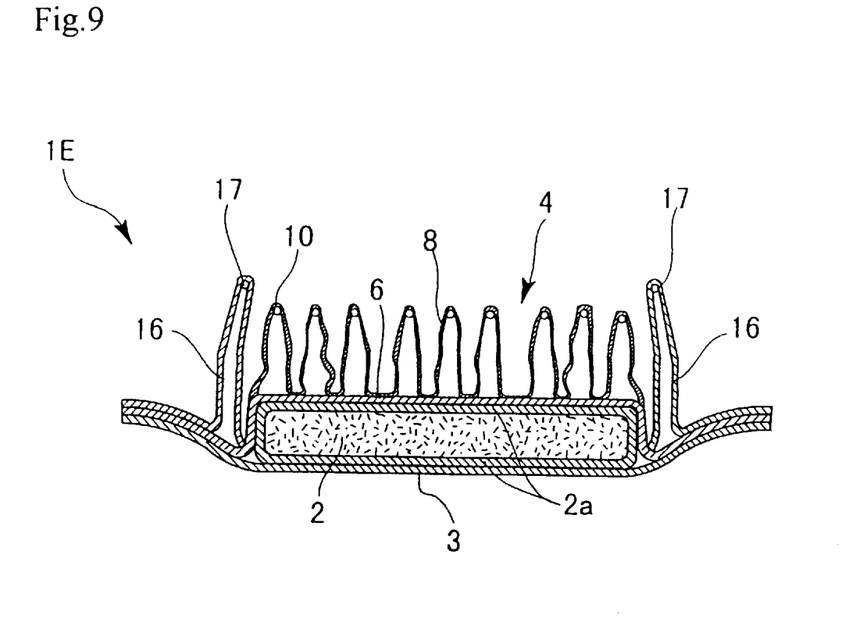
FIG. 9 is a (transversely) sectional view of the absorbent article of FIG. 8.
Figure 10:
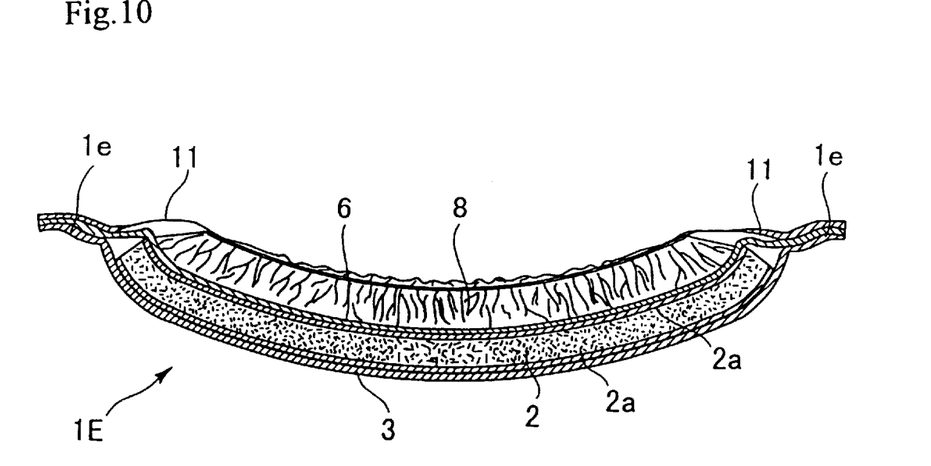
FIG. 10 is a (longitudinally) sectional view of the absorbent article of FIG. 8.

FIG. 8 is a perspective view showing a urine absorbing pad for an incontinent patient or old wearer (or absorbent article 1E), as a specific example of the absorbent article of the invention; FIG. 9 is a transverse section of FIG. 8; and FIG. 10 is a section taken in the longitudinal direction. The urine absorbing pad shown in FIG. 8 is preferably used for a female wearer, and is used on the inner side of an outer wear material such as disposable diaper or underwear.

This urine absorbing pad is constructed, as shown in FIG. 9, of the back sheet 3, the surface structure 4 and the absorbent core 2 sandwiched therebetween. The absorbent core 2 is formed by enveloping a mixture of pulverized pulp and highly absorbet polymer (or SAP) with a tissue paper 2a.

The ridges 8, as formed of the surface sheet 5 of the surface structure 4, are extended longitudinally of FIGS. 8 and 10 almost over the full length of the urine absorbing pad and are covered at their end portions with the cover sheets 11 and 11. These cover sheets 11, the support sheet 6 and the back sheet 3 are bonded to one another in the peripheral region A having no absorbent core 2. The cover sheets 11 form the pockets as in the absorbent article shown in FIG. 7.

This urine absorbing pad is wholly curved, as shown in FIG. 10, to fit along the crotch of the wearer by the elastic members 10 provided in the ridges 8. As a result, a number of wrinkles are formed on the surfaces of the ridges 8.

Adjacent to the ridges 8 in the transverse direction, in addition, there are formed stereoscopic gathers 16 and 16 for preventing the transverse leakage. With these stereoscopic gathers, it is possible to further prevent the transverse leakage of the excreted liquid. These stereoscopic gathers 16 and 16 are formed of liquid-impermeable sheets into the shape of band (or wall) which are provided with elastic members 17 and 17, on their upper side edges thereof, and are bonded to the upper face of the support sheet 6, on their lower side edges. Thus, the absorbent article 1E is provided with the stereoscopic gathers 16 and 16 which rise toward the wearer. Here, longitudinal end portions of the stereoscopic gathers 16 and 16 are hidden like the end portions of the ridges 8 by the cover sheets 11 and 11.

Here, the absorbent article of the invention can be used as not only a disposable diaper and an incontinent pad but also a sanitary napkin. In this case, the entire shape of the absorbent article can be variably modified according to the applications. For example, it may be modified to have a rectangular top plan shape.

As has been described hereinbefore, the absorbent article of the invention can bring its surface structure into close contact with the crotch to prevent the leakage. Moreover, the absorbent article having the ridges of the invention can be freely deformed according to the individual differences of the crotch so that it can fit the skin of the wearer to prevent the leakage more.

In the foregoing specification, the invention has been described in relation to preferred embodiments and many details have been set forth for the purpose of illustration. It will be apparent to those skilled in the art that the invention is susceptible to additional embodiments and that certain of the details described herein can be varied considerably without departing from the basic principles of the invention.

Further, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising: a surface structure having a liquid-permeable surface sheet located on a liquid-receiving side; a back sheet; and an absorbent core sandwiched between the surface structure and the back sheet, wherein, in an area including at least a centerline extending in a longitudinal direction of the absorbent article, the surface sheet is corrugated to form recesses and ridges extending in the longitudinal direction and alternating with each other in a transverse direction perpendicular to the longitudinal direction, and the ridges are given an elastically shrinking function in the longitudinal direction at least at their crests or vicinities thereof so that the surface structure is formed into a curved shape, wherein the surface structure further comprises a liquid-permeable support sheet located between the surface sheet and the absorbent core, and the support sheet is bonded to the recesses of the surface sheet, and a cushion layer is provided inside of the ridges such that the cushion layer is sandwiched between the surface sheet and the support sheet.

2. An absorbent article according to claim 1, wherein ridges in a center region including the longitudinally extending centerline are different in height from other ridges in two side regions outside of the center region.

3. An absorbent article according to claim 2, wherein cover sheets are provided to cover longitudinal end portions of the ridges.

4. An absorbent article comprising: a surface structure have a liquid-permeable surface located on a liquid-receiving side; a back sheet; and an absorbent core sandwiched between the surface structure and the back sheet, wherein, in an area including at least a centerline extending in a longitudinal direction of the absorbent article, the surface sheet is corrugated to form recesses and ridges extending in the longitudinal direction and alternating with each other in a transverse direction perpendicular to the longitudinal direction, and the ridges are given an elastically shrinking function in the longitudinal direction at least at their crests or vicinities thereof so that the surface structure is formed into a curved shape, wherein the surface structure further comprises a liquid-permeable support sheet located between the surface sheet and the absorbent core, and the support sheet is bonded to the recesses of the surface sheet, elastic members extending in the longitudinal direction are attached to the crests of the ridges of the surface sheet so as to extend along the crests and give the elastically shrinking function thereto, and a cushion layer is provided inside of the ridges such that the cushion layer is sandwiched between the surface sheet and the support sheet.

5. An absorbent article according to claim 4, wherein ridges in a center region including the longitudinally extending centerline are different in height from other ridges in two side regions outside of the center region.

6. An absorbent article according to claim 5, wherein cover sheets are provided to cover longitudinal end portions of the ridges.

7. An absorbent article according to claim 4, wherein cover sheets are provided to cover longitudinal end portions of the ridges.

* * * * *